United States Patent [19]

Hidasi et al.

[11] Patent Number: 4,963,584
[45] Date of Patent: Oct. 16, 1990

[54] PYRETHROIDAL COMPOSITION COMPRISING MORE THAN ONE ACTIVE INGREDIENTS

[75] Inventors: György Hidasi, Budapest; István Székely, Dunakeszi; Béla Bertók, Budapest; Sándor Zoltán, Budapest; Lajos Nagy, Szentendre; Antal Gajári, Budapest; Éva Somfai, Budapest; Ágnes Hegedüs, Budapest; László Pap, Budapest; Ruldof Soós, Budapest; Erzsébet Radvány, Budapest; Sándor Botár, Budapest; Tamás Szabolcsi, Budapest, all of Hungary

[73] Assignee: Chinoin Gyogyszer es Vegyeszeti Termekek Gyara Rt., Budapest, Hungary

[21] Appl. No.: 371,650

[22] Filed: Jun. 19, 1989

Related U.S. Application Data

[63] Continuation of Ser. No. 918,129, filed as PCT NU86/00003 on Jan. 16, 1986, published as WO86/04215 on Jul. 31, 1986, abandoned.

[30] Foreign Application Priority Data

Jan. 16, 1985 [HU] Hungary ................. 158/85
Jan. 8, 1986 [HU] Hungary ................. 74/86

[51] Int. Cl.$^5$ ............................................. A01N 37/34
[52] U.S. Cl. ............................................. 514/521
[58] Field of Search ................................. 514/521

[56] References Cited

U.S. PATENT DOCUMENTS 4,024,163  5/1977  Elliott et al. ............ 260/347.4
4,287,208  9/1981  Fuchs et al. ............ 424/304
4,308,279  12/1981  Smeltz .................... 424/304
4,427,598  1/1984  Mason et al. ............ 260/465 D

FOREIGN PATENT DOCUMENTS 0067461  5/1982  European Pat. Off. .
56-57755  5/1981  Japan .................... 514/521
56-57756  5/1981  Japan .................... 514/521

OTHER PUBLICATIONS

Ackermann et al, *Pesticide Science*, vol. 11, 169–179 (1980).
Elliott et al, *Pesticide Science*, vol. 9, 112–116 (1978).
Wood Mackenzie & Co., Ltd., N.Y., *Agrochemical Service*, pp. 44, 76, 81, 132, 136 (1986).

Primary Examiner—Allen J. Robinson
Attorney, Agent, or Firm—Herbert Dubno; Myers Jonathan

[57] ABSTRACT

According to the present invention there is provided an insecticidal composition containing more than one active ingredients which comprises as active ingredient in an amount of 0.001–99% by weight a synthetic pyrethroid of the general Formula I

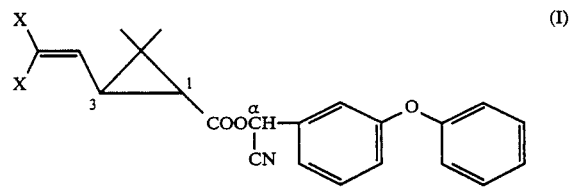

wherein X stands for chlorine or bromine—namely out of the eight possible isomers at least 95% of a 55:45–25:75 mixture of the enantiomer-pairs Ia:Ib, wherein Ia is 1RcisS+1ScisR and Ib is 1RtransS++1-StransR—if desired, in admixture with an activator and/or with an amount of up to 100% of an auxiliary agent, preferably an antioxidant, stabilizer, wetting agent, emulsifying agent, dispersing agent, antifoam agent, diluent, carrier, and/or filler.

The advantage of the insecticidal composition of the present invention is that it is less toxical towards warm-blooded animals and useful parasites and is therefore much less harmful to the environment.

5 Claims, No Drawings

PYRETHROIDAL COMPOSITION COMPRISING MORE THAN ONE ACTIVE INGREDIENTS

This is a continuation of co-pending application, Ser. No. 06/918,129 filed as PCT/HU86/00003 on Jan. 16, 1986, published as WO86/04215 on Jul. 31, 1986 now abandoned.

CROSS REFERENCE TO RELATED APPLICATION

This is a national phase of PCT/HU86/00003 filed Jan. 16, 1986 and based upon Hungarian national application No. 158/85 of Jan. 16, 1985 FA 74/86 of Jan. 8, 1986. The application is also related to PCT/HU86/00004.

FIELD OF THE INVENTION

This invention relates to insecticidal compositions comprising more than one pyrethroid active ingredients, the use thereof, the active ingredients and a process for the preparation of the same.

BACKGROUND OF THE INVENTION

In the present specification the spatial configuration of the substituents related to the chiral carbon atom denoted with "α" is characterized by "S" and "R" respectively. The designations "cis" and "trans", respectively, mark the position of the substituents attached to carbon atom "3" of the cyclopropane ring related to the spatial configuration of the substituents of carbon atom "1". The absolute spatial configuration of the substituent attached to carton atom "1" is denoted with the prefix "1R" and "1S", respectively.

In the present specification the various enantiomers and enantiomer-pairs are designated with the following abbreviations:
Ia: mixture of 1RcisS and 1ScisR
Ib: mixture of 1RtransS and 1StransR
Ic: mixture of 1RcisR and 1ScisS
Id: mixture of 1RtransR and 1StransS
If: 1RcisS
Ig: 1RtransS
Ih: 1ScisR
Ii: 1StransR Of the compounds of the Formula I

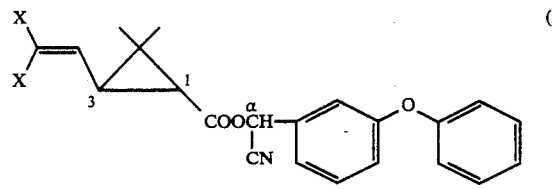

the following are commercially available;
"Cypermethrin" of the Formula II

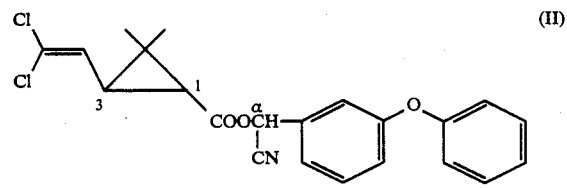

comprising all isomers;
"Alphamethrin" of the Formula II comprising only the 1RcisS and 1ScisR isomers;

"Deltamethrin" of the Formula III

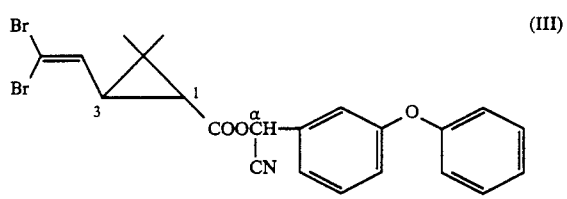

comprising only the 1RcisS isomer.

Selection of the possible isomers on the basis of insecticidal effect is based on the experimental fact that—particularly according to tests carried out on *Musca domestica* species—certain isomers have proved to be highly and outstandingly toxic on certain insects and it was the obvious trend to put the most active isomers on the market or to synthesize the same [Pest. Sci. 7, 273 1976].

It is known that the pyrethroids of the Formula II (known under the generic name "cypermethrin", belong to the valuable family of synthetic pyrethroids and are useful as insecticides (Hungarian patent No. 170,866). This compound may be prepared by reacting m-phenoxybenzaldehyde cyanohydrine with cyclopropane carboxylic acid chloride in the presence of a base [Pestic. Sci 6, 537, 1975]. The product thus obtained consists of eight stereoisomers i.e. of a mixture of four enantiomer-pairs. If a 60:40 mixture of trans and cis cyclopropane carboxylic acid chlorides is used, the mixture contains 18–19% of enantiomer-pair Ia, 21–22% of enantiomer-pair Ic, 26–27% of enantiomer-pair Ib and 33–34% of enantiomer-pair Id.

According to prior art the stereoisomers of cypermethrin show different biological activities. It is generally accepted that the activity of molecules comprising cis cyclopropane carboxylic acids is superior to that of the corresponding trans derivatives [Pest. Sci. 7, 273, 1976].

In the comparative biological tests of various pyrethroids [Pest Sci. 9, 112–116, 1978] the cis and trans stereoisomers—including the cypermethrin stereoisomer-pairs—were evaluated together.

The comparative tests were carried out in *Musca domestica* L. and *Phaedon cochleariae* Fab species. Concerning the chloro derivatives from the trans isomers activity data of 1RtransS (Ig) and 1RtransR were disclosed. The said data show that—while the 1RtransS isomer possesses a strong activity—the 1RtransR isomer is considerably less active [according to the test the activity related to bioresmethrin (100) amounts to 1400 and 81, respectively, on *Musca domestica* and to 2200 and 110, respectively, on *Phaedon cochlearia*]. It was disclosed further that the activity of a mixture of both tested isomers was lower than the calculated value. Thus the isomers showed an antagonism rather than the expected synergism and the rate of antagonism amounted to 1.42 and 1.46 on house fly and mustard beetle, respectively.

As a result of the said tests and publications the trans isomers and mixtures thereof were pushed to the background of biological interest and research was focused to active cis derivatives and mixtures thereof. This led to the development of alphamethrin [isomer mixture of 1RcisS and 1ScisR (Ia) of the chloro derivative] and decametrine [comprising the only 1RcisS isozer (If) of the bromo derivatives].

For this reason several procedures are known for the preparation of mixtures enriched in the cis isomers from known cypermethrin isomer mixtures.

DESCRIPTION OF THE INVENTION

According to an aspect of the present invention there is provided an insecticidal composition containing more than one active ingredients which comprises as active ingredient in an amount of 0.001–99% by weight a synthetic pyrethroid of the general Formula I (wherein X stands for chlorine or bromine)—namely out of the eight possible isomers at least 95% of a 55:45–25:75 mixture of the enantiomer-pairs Ia:Ib, wherein Ia is 1RcisS+1ScisR and Ib is 1RtransS+1StransR—if desired in admixture with an activator and/or with an amount of up to 100% of an auxiliary agent, preferably an antioxidant, stabilizer, wetting agent, emulsifying agent, dispersing agent, antifoam agent, diluent, carrier, and/or filler.

The present invention is based on the discovery that the isomeric mixture Ia+Ib possesses valuable and advantageous biological properties. The said properties are surprising and unaforeseen, although extended research work has already been performed in the field of pyrethroids of the Formula I and a number of publications and patents have been published.

It is known further that mixtures enriched in cis isomers can be prepared by means of crystallization from solutions comprising other isomers [C.A. 95, 1981; KOKAI No. 57755/81]. A substantially pure 1:1 mixture of the 1lRcisS and 1ScisR isomers may be separated by using suitable solvents from a mixture comprising the other cis isomers too (British patent specification No. 2,064,528). The isomeric mixture Ia is described to be very active. Special, so-called "high cis" syntheses have been elaborated for the preparation of cis-cyclopropane carboxylic acid intermediates comprising cis isomers above a certain limit (about 50%), but these methods were rather expensive [Angew. Chem. Ie, 24, 11, 996 1985].

The present invention is based on the recognition that when using a combination of the 1RtransS isomer Ig (being the most active trans isomer of the compounds of the Formula II) and the 1StransR isomer Ii (being ranged among the less active isomers from the remaining seven isomers) no antagonism characteristic for the earlier published isomer-pairs is observed.

Moreover a synergistic effect occurs over the additive effect of the pure Ig and Ii isomers when used per se.

The above discovery enables a new type of selection from the isomers of synthetic pyrethroids in order to develop a new active ingredient type having outstanding properties. The said new active ingredient shows various advantages over hitherto known isomer selections:
lower toxicity on a warm-blooded species and humans;
more economical manufacturing process;
smaller damages caused to useful parasites and bees.

The new compositions comprising the isomer-mixture Ib are described and claimed in our co-pending patent application Ser. No. 06/916,546, (based upon PCT/HU86/0004).

The present invention is based on the further discovery that the biological order of succession of biological activity previously observed for the individual isomers and the already known rules described for the isomer-pairs are not absolutely relevant for other isozer-pairs.

Thus we have tried to compare and simultaneously test the 1RtransS+1StransR enantiomer-pair Ib—which was found to be active by our experiments—with other isomers. The comparison has shown that synergism observed between the members of enantiomer-pair Ib (i.e. Ig and Ii) does not take place between the members of the corresponding cis enantiomer-pair Ia (i.e. If and Ih).

The present invention is based on the further discovery that while from the 1RcisS (If) and 1RtransS (Ig) isomers it is generally the If isomer which is the more active, on certain specii the biological activity of the enantiomer-pairs Ia and Ib proves to be opposite.

As a result of the aforesaid we have come to the surprising recognition that when using simultaneously the enantiomer-pairs Ia and Ib a synergistic effect is observed, i.e. the effect of the combination is superior to that of the additional effect of both enantiomer-pairs when used per se.

It has been found that the synergistic biological effect of mixtures Ia+Ib is not limited to such mixtures in which Ib is more active than Ia. Thus on Colorado potato beetle (*Leptinotersa decemlineata*) the use of the two enantiomer-pairs results in a significant synergism. The said results are disclosed in details in the examples.

Based on the above recognitions we have performed a new selection from the already known isomer mixtures and this led to the new composition of the present invention.

In addition to the synergistic effect the composition of the present invention has a number of further advantages too and for this reason it is an outstanding product. It is very important that the compositions of the present invention are less toxic towards mammals than the hitherto known compositions of similar efficiency. This is unambiguously proved by the so-called selectivity index (517 and 747 respectively) which is the quotient of the approximate $LD_{50}$ values measured on rats p.o. (280 and 355 mg/kg, respectively) and on house fly topically (0.54 and 0.48 mg/kg, respectively). The said selectivity index of Ia amounts to 50/0.45=111.

The synergistic effect may be observed on mites too (see biological Example No. 19), thus the compositions are also useful as acaricidal agents. The compositions of the present invention show a low toxicity towards bees and do not damage useful entomophages and parasites (biological Examples 25 and 26). The said advantageous properties are due to the repellant effect, preferable persistence and suitable inherent activity of the active ingredient.

The above properties enable the use of the mixture of the enantiomer-pairs of the present invention in integrated plant protecting technology (IPM=Integrated Pest Management).

The economical advantages of the compositions of the present invention are at least as important as the biological efficiency. The preparation of a pure cis enantiomer-pair Ia requires very expensive synthetic methods or involves the loss of the trans components formed in the reaction mixture. On the other hand the present invention enables the use of practically all the components Ia and Ib from the reaction mixture formed by the most economical syntheses. (The rate of efficiency depends naturally on the particular syntheses used and the ratio of the components Ia and Ib of the mixture).

The insecticidal compositions of the present invention comprising the isomer-pairs Ia and Ib in admixture with known additives may be formulated in forms suitable for direct use.

The composition of the present invention may be ULV (ultra-low-volume) compositions, spray, dispersible powders, granules, wettable and other powders, stable emulsions etc. The said compositions are suitable for the pesticidal treatment of vegetables, grape fields, orchards, fields of cereals and other large scale cultures. Due to the low toxicity the compositions of the present invention are particularly suitable for combating flying insects and pests having a hidden mode of life in households, walls of stables for the treatment of pasture etc.

According to a further aspect of the present invention there is provided the use of the said insecticidal compositions. It is preferred to use the said compositions under field conditions at a rate of 2-25 g of active ingredient per hectare.

The insecticidal compositions of the present invention may comprise in addition to the isomer-pairs Ia+Ib activators and further synergists, e.g. piperonyl butoxide. The said additives increase strengthen the efficiency of the active ingredient without increasing the toxicity on warm-blooded species.

According to a preferred embodiment of the present invention there are provided dispersible granules comprising 1-99% by weight of the active ingredient in admixture with 99-1% by weight of suitable additives. As auxiliary agent e.g. 0.1-1% by weight of anionic and/or non-ionic surfactants may be used, such as alkali salts of alkyl-aryl sulfonic acids, alkali salts of condensation products of alkyl aryl sulfonic acids and formaldehyde, alkyl-aryl-polyglycol ether, sulfated long chained alcohols, polyethylene oxides, sulfated fatty alcohols, fatty acid polygylcol esters and various other commercially available surfactants.

The insecticidal compositions of the present invention may also be formulated in the form of concentrates comprising preferably 5-50% by weight of the active ingredient in admixture with 50-95% by weight of additives which enable the formation of a stable emulsion when emulsifying the emulsion concentrate in or in the presence of water.

As additive 1-20% by weight of a tenside and/or 0.1-5% by weight of a stabilizing agent may be used and the mixture may be preferably filled up to 100% with an organic solvent.

It is preferred to use as tenside a mixture of anionic and non-ionic tensides. The following tensides may be preferably applied: calcium salts of alkyl aryl sulfonic acids, mono and diesters of phosphoric acid, nonyl and tributyl phenol polyglycol ethers, adducts of fatty alcohols and ethylene oxide, fatty acid polyglycol esters, ethylene oxide—propylene oxide block polymers etc.

As solvent preferably mixtures of aromatic hydrocarbons (e.g. xylenes), cyclohexanol, butanol, methyl ethyl ketone, isopropanol etc. may be used.

The compositions of the present invention may also comprise further synergists which enable the reduction of the amount of the active ingredient. For this purpose preferably piperonyl butoxide may be applied.

According to a further aspect of the present invention there is provided a process for the preparation of an insecticidal active ingredient comprising out of the eight possible isomers of synthetic pyrethroids of the Formula I (wherein X stands for chlorine or bromine) substantially only a 55:45-25:75 mixture of enantiomer-pairs Ia:Ib—wherein Ia is 1lRcisS and 1ScisR and Ib is 1RtransS and 1StransR—with comprises.

a. preparing from a mixture comprising in addition to the isomer-pairs Ia+Ib other possible isomers too and/or comprising the isomer-pairs Ia+Ib in a ratio other than the desired values a saturated solution with a protic or apolar aprotic inert organic solvent, seeding the solution with a seeding crystal consisting of a 55:45-25:75 mixture of enantiomer-pairs Ia and Ib, and isolating the crystals precipitating at a temperature between 30° C. and −30° C.; or b. seeding a melt of a mixture comprising in addition to the isomer-pairs Ia+Ib other isomers too and/or comprising the isomer-pairs Ia+Ib in a ratio other than the desired value at a temperature between 10° C. and 60° C. with a seeding crystal comprising a 55:45-25:75 mixture of enantiomer-pairs Ia and Ib, allowing the solution to crystallize at a temperature between 30° C. and −10° C. and if desired suspending the mixture thus obtained at a temperature between −10° C. and −20° C. in a protic or apolar aprotic inert organic solvent and isolating the precipitated crystals; or c. adding to a solution or a melt of a mixture comprising in addition to the isomer-pairs Ia+Ib other isomers too and/or comprising the isomer-pairs Ia+Ib in a ratio other than the desired value an enantiomer-pair Ia or Ib in such an amount that the solution or the melt should contain the isomers in a ratio of 55:45-25:75 and if desired performing crystallization according to variant a. or b.; or d. admixing enantiomer-pairs Ia and Ib in the desired ratio—if desired in the presence of a protic or apolar aprotic organic solvent—homogenizing the mixture and performing crystallization—if desired after the seeding step according to variant a.

According to variants a of the process of the present invention one may preferably proceed by using a $C_{1-12}$ hydrocarbon, $C_{1-6}$ chlorinated hydrocarbon, $C_{1-5}$ dialkyl ether or $C_{1-10}$ alcohol as organic solvent. The said solvents may be straight or branched chained, and cyclic and alicyclic, respectively.

It is preferred to carry out seeding with a seeding crystal in the presence of an antioxidant—particularly tertiary butyl hydroxy toluene or 2,2,4-trimethyl-quinoline—and to use ethanol, isopropanol petrolether or hexane as solvent.

One may proceed preferably by accomplishing crystallization under slow cooling.

According to a preferred form of realization of the process of the present invention a mixture of 60% of trans and 40% of cis cypermethrin enantiomer-pairs (18.2% of Ia, 26.8% of Ib, 21.8% of Ic and 33.2 % of Id; referred to further as Ie) is used as starting material. The said mixture is dissolved in isopropanol and the solution is seeded with seeding crystals consisting of a mixture of Ia and Ib in the presence of 0.01% of 2,2,4-trimethyl-quinoline or tertiary butyl hydroxy toluene. A crystalline product is obtained with an absolute yield of 35-40%, which melts at 63.5°-65° C., comprises the enantiomer-pairs Ia and Ib in a ratio of 40:60 and contains enantiomer-pairs Ic and Id as contamination in an amount of 5%. The products thus obtained may be recrystallized as described above. Thus the mixture of enantiomer-pairs Ia and Ib can be prepared with a purity above 99%.

Similar results are obtained when recrystallizing mixtures of other cis/trans ratio.

The cypermethrins used as starting material may be prepared by esterifying the mixture of cyclopropane carboxylic acids of suitable cis/trans ratio.

In the following Table the melting points of mixtures of various cis/trans ratio are disclosed.

| Ia/Ib | 25:75 | 30:70 | 40:60 | 50:50 | 55:45 |
|---|---|---|---|---|---|
| m.p.:°C. | 67-7.5 | 65-68 | 63.5-65 | 60.5-62 | 61.5-64 |

The practical feasibility in the desired direction of the crystallization step strongly depends on the parity of the starting cypermethrin mixture. If the active ingredient content is lower than 95%, the yields decrease. Tarry contaminations may even inhibit crystallization.

The crystallization of the mixture of enantiomer-pairs Ia and Ib according to the present invention may be carried out in the absence of a solvent too. Thus cypermethrin of the composition Ie may be seeded with crystals consisting of Ia and Ib. In a refrigerator the mixture of Ia and Ib precipitates within a week. The crystals are isolated by adding ethanol cooled to $-20°$ C. to the mixture and filtering the crystals.

The mixture of enantiomer-pairs Ia+Ib according to the present invention may also be prepared by admixing and/or crystallizing Ia and Ib or various amounts thereof or by admixing and/or crystallizing a mixture of Ia and Ib, or calculated amount of Ib, respectively.

The biological activity of the products according to the present invention is tested on various insect specii. In the test methods the effect of stereoisomers used as reference standard and prepared by known methods—e.g. by chromatographical separation or by chromatographical separation of cypermethrins prepared from chiral acids—is disclosed as well.

Industrial applicability

The insecticidal compositions of the present invention are harmless to environment and can be used particularly in household and stables for combating flying insects and pests having a hidden mode of life and also for the treatment of pasture.

Modes of Carrying out the Invention

Further details of the present invention are to be found in the following chemical and biological examples without limiting the scope of protection to the said Examples.

CHEMICAL EXAMPLES

Example 1

100 g of cypermethrin (consisting according to gas chromatography of a mixture of 18.2% of Ia, 21.8% of Ic, 26.8% of Ib and 33.2% of Id), 0.2 g of potassium hydroxide and 0.2 g of 2,6-di-tertiary butyl-4-methyl-phenol are dissolved in 2000 ml of isopropanol under constant stirring at 45.0° C. The solution is slowly cooled to 30° C., clarified with activated charcoal and filtered at 30° C. The colourless solution is seeded with a crystal consisting of 60% of Ib and 40% of Ia and the mixture is stirred at $-10°$ C. for 24 hours. The precipitated product is filtered, washed with isopropanol and dried in vacuo. Thus 36.02 g of a snow-white crystalline product are obtained. M.p.: 62°-65° C. (non-corrected value). According to GC and TLC analysis the product contains 37% of Ia an 58% of Ib isomers. Yield: 76% (related to the Ia+Ib isomer content of the cypermethrin starting material).

Ia isomer $R_f = 0.25$; Ib isomer $R_f = 0.20$.

After recrystallization from isopropanol 32 g of the product are obtained as first crops. M.p.: 63.5°-65.0° C.; the product consists of 39.5% of Ia and 59.5% of Ib.

IR (KBr) $\nu_{c=o}$: 1730, 1735 cm$^{-1}$

NMR (CDCl$_3$) $\delta$(ppm): 1.05-2.45 m (8H); 5.6, d,J=8 Hz (=CH trans 0.6H); 6.14, d, J=8 Hz (=CH cis 0.4H); 6.35, d, (1H); 6.85-7.60 m, (9H)

Example 2

100 g of cypermethrin (27.8% of Ia, 21.8% of Ib, 32.1% of Ie and 18.2% of Id, 0.2 g of potassium hydroxide and 0.2 g of 2,6-di-tertiary butyl-4-methylphenol are dissolved in 2000 ml of isopropanol under stirring at 45° C. The solution is clarified with activated charcoal and filtered at 30° C. The colourless solution is seeded with a seeding crystal consisting of 20% of Ib and 80% of Ia and stirred at $-10°$ C. for 36 hours. The precipitated product is filtered, washed with isopropanol and dried in vacuo. Thus 30 g of snow-white crystalline product are obtained, m.p.: 66°-73° C. According to gas chromatography the product contains 77% of Ia+19% of Ib, purity 96% (TLC, see Example 1). After recrystallization from isopropanol as first generation 26.5 g of a snow-white crystalline product are obtained, m.p.: 70°-73° C., containing 81.5 of Ia+18% of Ib (GC analysis).

IR (KBr)$\nu_{c=o}$: 1730 cm$^{-1}$

NMR (CDCL$_3$)$\delta$ (ppm): 1.05-2.45 m (8H); 5.60 d J=8 Hz (=CH trans 0.2H ); 6.14 d J=8 Hz (=CH cis 0.8H); 6.35 d (ArCH 1H) 6.85-7.60 m (9H).

Example 3

100 g of colorless clearly transparent oily cypermethrin (18.2% of Ia, 21.8% of Ic, 26.8% of Ib and 32.2% of Id) are seeded with a seeding crystal consisting of 60% of Ib and 40% of Ia and the solution is allowed to crystallize at 7° C. for a week. The mixture is suspended in 100 ml of a 1:1 mixture of isopropanol and diisopropyl ether and filtered at $-15°$ C. The crystals are washed with isopropanol and dried in vacuo. Thus 40.1 g of a white crystalline product are obtained, containing 37.5% of Ia and 59% of Ib, m.p.: 62.5°-65° C. Yield 86%. After recrystallization from isopropanol as first generation 36 g of a snow-white crystalline product are obtained, m.p.: 63.5°-65° C., consisting of 40% of Ia and 60% of Ib (GC). The IR and NMR are identical with those disclosed in Example 1.

Example 4

100 g of cypermethrin (18.2% of Ia, 21.8% of Ic, 26.8% of Ib, 33.2% of Id) and 0.05 g of 2,6-ditertiary butyl-4-methyl-phenol are dissolved in 100 ml of diisopropyl ether under constant stirring at 0° C. and the solution is clarified with 2 g of activated charcoal. The solution is filtered and seeded at $-15°$ C. with a seeding crystal consisting of 60% of Ib and 40% of Ia. The mixture is allowed to crystallize for 72 hours, the crystals are filtered, washed with diisopropyl ether and isopropanol and dried Thus 38 g of a snow-white crystalline product are obtained, yield 62°-65° C., comprising 37.5 g % of Ia and 58% of Ib. Yield 80.6%. After recrystallization from isopropanol as first generation 35 g of a snow-white crystalline product are obtained, m.p.: 63.5°-65° C., the ratio of the Ia:Ib isomers=40:60. The physical constants are identical with those disclosed in Example 1.

Example 5

10 g of samples of the product obtained according to Example 2(the ratio of the Ia:Ib isomers=4:1) are admixed with 4.60 g, 6 g, 10 g, 16.67 g and 22.0 g of pure seeding crystals of Ib, respectively, and the mixtures thus obtained are recrystallized as described in Example 1 from a 10-fold amount of isopropanol, each. The composition and melting point of the products thus obtained are shown in the following Table.

| Ia:Ib | M.p.: (°C.) |
|---|---|
| 55:45 | 61.5–64 |
| 5:5 | 60.5–62 |
| 4:6 | 63.5–65 |
| 3:7 | 65–68 |
| 25:75 | 67–71.5 |

Example 6

10 g samples of pure crystalline isomer-pair Ia are admixed with 8.20 g, 10.00 g and 15.00 g of pure crystalline isomer-pair Ib, respectively, and the mixtures are homogenized. The crystal mixtures thus obtained comprise the substances Ia+Ib in a ratio of 55:45, 50:50 and 40:60, respectively. M.p.: 61.5°–64° C., 60.5°–62° C. and 63.5°–65° C., respectively.

Example 7

10 g samples of pure crystalline isomer-pair Ia are dissolved in 10-fold amount of isopropanol and to each sample 23.43 g and 30.0 g of pure crystalline isomer-pair Ib are added, respectively. The solutions are crystallized. The precipitated white crystalline products (m.p.: 65°–68° C. and 67°–71.5° C., respectively) comprise the Ia:Ib isomers in a ratio of 30:70 and 25:75, respectively. The product thus obtained can be formulated as plant protecting agent and is a useful insecticidal active ingredient.

FORMULATING EXAMPLES

Example 8

To 166.2 g of perlite ($d_{max}=120$ μm) 0.8 g of synthetic silicic acid (Aerosil 300) are added in a fluidizing rapid stirrer. 20 g of a cypermethrin mixture of enantiomer-pairs Ia:Ib=4:6 and 2 g of fatty alcohol polyglycol ether are added so that the mixture is uniformly homogenized. The powder mixture is ground first in a mechanical mill and afterwards in an air flow mill, whereupon 5 g of octyl phenol polyglycol ether (EO=20) and 2 g of sulfosuccinate are added in a rapid stirrer. The wettable powder mixture (WP) thus obtained is subjected to suspension stability test. Wetting time=23 seconds; floatability=89% (standard WHO method).

Example 9

3 g of a mixture of cypermethrin enantiomer-pairs Ia:Ib=3:7 and 0.3 g of fatty alcohol polyglycol ether are applied in a homogenizing apparatus onto talc ($d_{max}=15$ μm) adjusted to the pH value of 6.5 with a buffer of 0.8 of synthetic silicic acid (Aerosil 200) and 193.9 g of potassium and sodium phosphate. To the mixture 1 g of dioctyl sulfosuccinate and 1 g of fatty alcohol polyglycol ether sulfonate are added under stirring and the mixture is ground to an average particle size of 20 μm. Thus a thin flowable powder mixture is obtained.

Example 10

5 g of a mixture of cypermethrin enantiomer-pairs Ia:Ib =55:45 are dissolved in a mixture of 21.25 g of xylene and 42.5 g of n-propanol under slow stirring. To the solution a mixture of 4 g of ethoxylated alkyl phenol+calcium salt of linear alkyl aryl sulfonate and a mixture of 6 g of ethoxylated amine+alkali salt of linear alkyl aryl sulfonate is added under stirring until all the materials are completely dissolved, whereupon 21.25 g of water are added. Thus a transparent solution is obtained which maintains its properties at a temperature between 0° C. and 50° C. for long period of time. The solution can be optionally diluted with water at any rate under the formation of an emulsion having a droplet-size of 0.8–1.5 μm.

Example 11

5 g of a mixture of cypermethrin enantiomer-pairs Ia:Ib=25:75 are dissolved in a mixture of 75 g of xylene and 10 g of an aliphatic oil whereupon under slow stirring a mixture (7.5 g) of ethoxylated alkyl phenol+calcium salt of linear alkyl aryl sulfonate and also a mixture (2.5 g) of ethoxylated fatty acid+linear alkyl aryl sulfonate salt are added. When measured according to the method of CIPAC the emulsion concentrate proves to be stable after 170 hours.

Example 12

In a mechanical granulator a 50:50 mixture of the Ia and Ib cypermethrin enantiomer-pairs is admixed with 1500 g of polycyrboxylate alkali salt, 500 g of sodium dodecyl benzene sulfonate, 500 g of saccharose and 7200 g of China-clay. The powder mixture is admixed with 8300 ml of water by using a stirrer of large shearing strength (v=10 m/sec) and subjected to spray drying. The distribution of particle size is as follows: 0.1–0.4 mm=95%. The floatability amounts to 98% (according to the WHO method).

Example 13

Emulsifiable concentrates (EC) are prepared by admixing the following components:

| Component | Amount, kg/kg |
|---|---|
| 10 EC | |
| Isomer-pairs Ia:Ib = 40–60 | 0.105 |
| Cyclohexanol | 0.290 |
| Atlox 3386 B | 0.020 |
| Atlox 3400 B | 0.045 |
| Odourless mineral oil | 0.540 |
| 5 EC | |
| Isomer-pairs Ia:Ib = 40–60 | 0.050 |
| Cyclohexanol | 0.290 |
| Atlox 3386 B | 0.020 |
| Atlox 3400 B | 0.045 |
| Odourless mineral oil | 0.595 |

BIOLOGICAL EXAMPLES

Example 14

In Table 1 the activity of various stereoisomers of cypermethrin on house fly (*Musca domestica*) is shown.
The test is carried out as follows:
The active ingredient is dissolved in a 1:2 mixture of oil and acetone; filter paper discs (Whatman No. 1, diameter 9 cm) are impregnated with the solutions of the corresponding stereoisomers and enantiomer-pairs, respectively. The acetone is allowed to evaporate, whereupon the insects are exposed to filter paper discs placed in Petri-dishes. Three parallels are used or each dose and 15 insects are placed into each Petri-dish. The percental mortality is determined after 24 hours. The corrected percent mortality is calculated by means of the Abbot Formula.

TABLE 1

| Cypermethrin stereoisomer | Dose (mg/disc) | | | | |
|---|---|---|---|---|---|
| | 0.04 | 0.11 | 0.33 | 1.00 | 3.00 |
| | 24 hours' mortality /%/ | | | | |
| If | 68 | 93 | 100 | 100 | 100 |
| Ia | 44 | 84 | 100 | 100 | 100 |
| Ig | 48 | 68 | 83 | 100 | 100 |
| Ib | 32 | 62 | 95 | 100 | 100 |
| Ia:Ib = 40–60 | 41 | 81 | 100 | 100 | 100 |

According to this test the activity of mixture Ia+Ib corresponds to that of the pure isomer Ia.

Example 15

It appears from Table 2 that the increased activity shown in Example 14 is due to the synergistic effect of the trans-isomers to *Tribolium confusum*.

TABLE 2

| Active ingredient | Dose (mg/disc) | | | |
|---|---|---|---|---|
| | 0.11 | 0.33 | 1.00 | 3.00 |
| | 24 hours' mortality % | | | |
| IScisR (Ih) | 0 | 38 | 80 | 100 |
| IRcisS (If) | 80 | 100 | 100 | 100 |
| Ia | 22 | 65 | 94 | 100 |
| IStransR (Ii) | 0 | 0 | 71 | 90 |
| IRtransS (Ig) | 70 | 92 | 100 | 100 |
| Ib | 64 | 89 | 100 | 100 |
| Ia:Ib = 40:60 | 61 | 89 | 100 | 100 |

In Example 18 it is shown on further insect species that the enantiomer-pair Ib of the present invention is more active than Ia. The increased activity manifests itself not only in the 24 hour' mortality but also in the fact that the toxical effect is exhibited more rapidly.

Example 16

In Table 3 the insecticidal effect of mixtures of enantiomer-pairs Ia and Ib of various ratio is shown on flour beetle (*bolium confusum*). The test method is that disclosed in Example 14.

TABLE 3

| Ia:Ib | Dose (mg/disc) | | | |
|---|---|---|---|---|
| | 0.02 | 0.06 | 0.25 | 1.00 |
| | 24 hour' mortality % | | | |
| 10:0 | 0 | 14 | 54 | 100 |
| 5:5 | 0 | 43 | 100 | 100 |
| 4:6 | 14 | 53 | 100 | 100 |
| 3:7 | 20 | 81 | 100 | 100 |
| 0:10 | 8 | 46 | 100 | 100 |

The above data clearly prove the synergism between enantiomer-pairs Ia and Ib.

Example 17

According to a further recognition of the present invention when the mixtures of enantiomer-pairs Ia and Ib are combined with conventional pyrethroide synergists (e.g. piperonyl butoxide, NIA 16388 etc.) the increase of activity is larger than the usual value (see Example 16).

In Table 4 the activity on Colorado potato beetle is shown.

The test method is as follows:

The test materials are dissolved in 2-ethoxyethanol (Cellosolve). One 0.3 μl drop of the solution is applied to the abdominal sterna of the imago. The treatment is carried out by using 2 parallels and 10 insects for each dose. Mortality is determined after 48 hours.

TABLE 4

| Active ingreident | Dose (ug/beetle) | | | |
|---|---|---|---|---|
| | 0.05 | 0.10 | 0.20 | 0.40 |
| | 24 hour' mortality % | | | |
| Ia | 50 | 55 | 75 | 80 |
| Ib | 0 | 25 | 75 | 85 |
| Ia:Ib = 4:6 | 45 | 60 | 70 | 80 |
| Ia:Ib = 3:7 | 45 | 65 | 75 | 85 |
| deltamethrin | 45 | 60 | 75 | 85 |
| cypermethrin | 0 | 20 | 45 | 75 |

Synergism is observed between enantiomer-pairs Ia and Ib, although on imago of Colorado potato beetle Ia is more active than Ib. Mixtures of enantiomer-pairs Ia and Ib exert the same activity a deltamethrin.

Example 18

The comparative test of Ia, Ib and a 40:60 mixture of Ia:Ib is carried out on bean weevil (*Acanthoscelides obtectus*), flour-beetle (*Tribolium confusum*), house fly (*Musca domestica*) and sheep maggot fly (*Lucillia sericata*). The test method described is Example 14 is used. The results are summarized in Table 5.

TABLE 5

| Species | Enantiomer pair | Dose (mg/disc) | | | | | |
|---|---|---|---|---|---|---|---|
| | | 0.02 | 0.07 | 0.22 | 0.67 | 2.0 | 6.0 |
| | | mortality % | | | | | |
| A. obtectus (imago) | Ia | 10 | 37 | 63 | 95 | 100 | 100 |
| | Ib | 32 | 55 | 87 | 100 | 100 | 100 |
| | Ia:Ib = 4:6 | 30 | 55 | 90 | 100 | 100 | 100 |
| T. confusum (imago) | Ia | 0 | 18 | 51 | 100 | 100 | 100 |
| | Ib | 14 | 73 | 100 | 100 | 100 | 100 |
| | Ia:Ib = 4:6 | 16 | 80 | 100 | 100 | 100 | 100 |
| M. domestica (imago) | Ia | 36 | 63 | 88 | 100 | 100 | 100 |
| | Ib | 0 | 18 | 67 | 100 | 100 | 100 |
| | Ia:Ib = 4:6 | 25 | 45 | 85 | 100 | 100 | 100 |
| L. sericata (imago) | Ia | 0 | 30 | 29 | 57 | 60 | 65 |
| | Ib | 22 | 55 | 70 | 75 | 100 | 100 |
| | Ia:Ib = 4:6 | 18 | 50 | 60 | 75 | 100 | 100 |

Example 19

Activity of cypermethrin stereoisomer-pairs as function of time on flour beetle (*T. confusum*).

Flour beetle (*T. confusum*) imagos are exposed in Petri-dishes according to the method described in Example 14. For each dose 3 parallels are used and 15 animals are applied for each parallel test. In each point of time the insects lying on their backs are counted and the percental results are expressed in Table 6.

TABLE 6

| Stereoisomer-pair and enantiomer- | Exposition time/minutes | Dose (mg/disc) | | | |
|---|---|---|---|---|---|
| | | 0.11 | 0.33 | 1.00 | 3.00 |
| | | % of insects showing toxical symptoms | | | |
| Ih | 30 | 0 | 0 | 0 | 0 |
| | 60 | 0 | 0 | 0 | 8 |
| | 120 | 0 | 0 | 0 | 67 |
| | 180 | 0 | 0 | 0 | 88 |

TABLE 6-continued

| Stereoisomer-pair and enantiomer- | Exposition time/minutes | Dose (mg/disc) | | | |
|---|---|---|---|---|---|
| | | 0.11 | 0.33 | 1.00 | 3.00 |
| | | % of insects showing toxical symptoms | | | |
| If | 30 | 0 | 0 | 48 | 64 |
| | 60 | 0 | 5 | 84 | 100 |
| | 120 | 0 | 40 | 100 | 100 |
| | 180 | 39 | 61 | 100 | 100 |
| Ia | 30 | 0 | 0 | 0 | 33 |
| | 60 | 0 | 0 | 16 | 88 |
| | 120 | 0 | 14 | 66 | 100 |
| | 180 | 10 | 49 | 100 | 100 |
| Ii | 30 | 0 | 0 | 0 | 15 |
| | 60 | 0 | 0 | 0 | 70 |
| | 120 | 0 | 0 | 0 | 100 |
| | 180 | 0 | 0 | 0 | 100 |
| Ig | 30 | 0 | 0 | 15 | 68 |
| | 60 | 18 | 34 | 98 | 100 |
| | 120 | 30 | 70 | 100 | 100 |
| | 180 | 34 | 84 | 100 | 100 |
| Ib | 30 | 0 | 0 | 47 | 61 |
| | 60 | 0 | 21 | 82 | 100 |
| | 120 | 28 | 100 | 100 | 100 |
| | 180 | 56 | 100 | 100 | 100 |
| Ia:Ib = 4:6 | 30 | 0 | 0 | 50 | 55 |
| | 60 | 15 | 85 | 85 | 100 |
| | 120 | 30 | 100 | 100 | 100 |
| | 180 | 55 | 100 | 100 | 100 |

Example 20

Imagos of flour-beetle (*T. confusum*) are treated in an analogous manner to Example 14. As synergist piperonyl butoxide is used in a dose of 0.5 mg/disc.

TABLE 7

| cypermethrin stereoisomer | Dose (mg/disc) | | | | |
|---|---|---|---|---|---|
| | 0.4 | 0.2 | 0.1 | 0.05 | 0.025 |
| | 24 hours' mortality % | | | | |
| Ia | 96 | 53 | 12 | 0 | 0 |
| Ia + PBO | 100 | 58 | 16 | 0 | 0 |
| Ia + Ib | 100 | 90 | 57 | 18 | 0 |
| Ia + Ib + PBO | 100 | 95 | 75 | 43 | 7 |

It may be seen that the mixture of enantiomers Ia and Ib can be synergized to a larger extent than enantiomer Ia (Ia:Ib=4.6).

Example 21

The active ingredients are dissolved in 2-ethoxyethanol and the solutions are applied in the form of 0.2 μl droplets onto the back of fall webworm (*Hyphantria cunea*) of $L_7$-$L_8$ larvae stage. The treated worms are placed on strawberry leaves in Petri-dishes. The test is carried out by using a doses, 2 parallels and 10 insects for for each dose. The killed worms are counted after 24 hours and the percental mortality rate is calculated. The results are summarized in Table 8.

TABLE 8

| Active ingredient | Dose (μg/larvae) | | | | |
|---|---|---|---|---|---|
| | 0.023 | 0.047 | 0.094 | 0.188 | 0.375 |
| | 24 hour' mortality % | | | | |
| Ia | 40 | 60 | 65 | 80 | 90 |
| Ib | 10 | 15 | 30 | 70 | 80 |
| Ia:Ib = 4:6 | 40 | 50 | 55 | 65 | 75 |
| cypermethrin | 0 | 10 | 25 | 50 | 75 |

Example 22

Leaves already infested with mites (*Tetranychus urticae*) were sprayed under Potter Tower. Mortality after 24 hours on the treated leaves was compared with the control.

TABLE 9

| Active ingredient | approx $LD_{50}$ /ppm/ |
|---|---|
| Ia | 0.056 |
| Ib | 0.340 |
| Ia:Ib = 4:6 | 0.060 |
| cypermethrin | 0.120 |
| deltamethrin | 0.185 |

Example 23

The 5 EC formulations prepared according to Example 13 are diluted 50×, 00×, 200×, 400×, 800× and 1600× with water and 0.5 ml doses are sprayed onto glass plates. After drying 10L decemlineata imagos are placed on each glass plate and the insects are covered with Petri-dishes. The tests are carried out by using 6 doses and 3 parallels for each dose. The killed insects are counted after 48 hours. The result are disclosed in Table 10.

TABLE 10

| 5 EC formulation | dilution | | | | | |
|---|---|---|---|---|---|---|
| | 1600x | 800x | 400x | 200x | 100x | 50x |
| | | | mortality % | | | |
| Ia | 0 | 27 | 53 | 63 | 87 | 97 |
| Ia:Ib = 4:6 | 0 | 33 | 53 | 73 | 80 | 93 |
| deltamethrin | 7 | 35 | 53 | 67 | 83 | 100 |
| cypermethrin | 0 | 17 | 33 | 50 | 67 | 83 |

Example 24

Glass plates are sprayed with 5 EC formulations prepared according to Example 13 in an analogous manner to Example 23. After drying 10 bean weevil (*Acanthoscelides obtectus*) imagos are placed on each plate and the insects are covered with Petri-dishes. The killed insects are counted after 24 hours. The test is carried out with 6 doses by using 3 parallels for each dose. The result are summarized in Table 11.

TABLE 11

| 5 EC formulation | dilution | | | | | |
|---|---|---|---|---|---|---|
| | 1600x | 800x | 400x | 200x | 100x | 50x |
| | | | mortality % | | | |
| Ia | 0 | 13 | 27 | 33 | 50 | 70 |
| Ia:Ib = 4:6 | 10 | 17 | 30 | 37 | 53 | 70 |
| deltamethrin | 7 | 13 | 20 | 37 | 57 | 75 |
| cypermethrin | 0 | 3 | 10 | 20 | 45 | 60 |

Example 25

15 bean plants infected with green peach aphids (*Myzus persicae*) at 6 days' age are cultivated in each pot. At 12 days' age the strongly and uniformly infected plants are selected and sprayed to run-off with emulsions freshly prepared from the formulation according to Example 13. Treatments are carried out with three doses (active ingredient 2.5, 5 and 10 ppm/ and four parallels are used /one pot per parallel). The second, fourth and eighth day after treatment the aphids are swept down from the plants to a white paper with a fine brush and the live insects are counted. The results are disclosed in Table 12.

TABLE 12

| 5 EC formulations | Concentration (ppm) | Average number of aphids per pot Days after treatment | | |
|---|---|---|---|---|
| | | 2 | 4 | 8 |
| Ia | 2.5 | 44 | 83 | 245 |
| | 5.0 | 22 | 29 | 90 |
| | 10.0 | 8 | 17 | 30 |
| Ia:Ib = 4:6 | 2.5 | 38 | 71 | 251 |
| | 5.0 | 21 | 32 | 82 |
| | 10.0 | 10 | 11 | 21 |
| deltamethrin | 2.5 | 26 | 47 | 137 |
| | 5.0 | 13 | 19 | 29 |
| | 10.0 | 6 | 11 | 23 |
| control | | 1850 | 2780 | 4120 |

Example 26

Tomato plants pre-cultivated in pots are sprayed with a suspension of the active ingredient formed with a mixture of acetone and water. The treated plants are placed into isolators and infected with L₃ stage *Leptinotarsa decemlineara* larvae. The percental ratio of paralysed larvae which fall down from the plants is determined after 6 hours. The results are disclosed in Table 13.

TABLE 13

| Concentration (ppm) | Ia | Ia:Ib = 4:6 |
|---|---|---|
| | % ratio of paralysed larvae | |
| 1000 | 100 | 100 |
| 200 | 100 | 100 |
| 40 | 46 | 75 |
| 8 | 18 | 60 |

Example 27

The treatments are performed on a 25 m² plot strongly infected with Colorado potato beetle. 10 plants per plot are specially marked on which the Colorado potato beetles were counted previously. (During assessment of the number of pests only adults of the second Summer generation are taken into consideration, because at the point of time of the test the ratio of larvae of stages L₃ and L₄ is negligible). Treatment is accomplished on 25 m² plots at a dose of 10 g of active ingredient/ha with aqueous suspensions of the formulations according to Example 10 and three parallels are used. The test is evaluated by counting the live insects on the marked plants. The average values of three parallel tests are disclosed in Table 14.

TABLE 14

| 5 ME formulation | Average number of live insects (10 plants) Time elapsed after treatment (in days) | | | |
|---|---|---|---|---|
| | 0 | 1 | 3 | 9 |
| Ia | 171 | 11 | 9 | 25 |
| Ia:Ib = 4:6 | 213 | 8 | 4 | 22 |
| Deltamethrin | 181 | 7 | 10 | 19 |
| Control | 211 | 206 | 179 | 183 |

Example 28

Residual contact test on adults of *Aphidinus matricariae*. Adults of *A. matricariae* are exposed to residues of the active ingredients freshly applied on glass plates forming cages, then the survivors are counted.

Treatment: test product and control treated with water.

Replicates: at least 3. Plot size (net): 1 cage.

Parasites of known age (24 hours) are used.

The products are applied at 5,1 ppm concentration, to each of the glass plates.

10 females of *A. matricariae* are introduced into each cage and supplied with honey as food. The number of females surviving exposure is determined after 1,5 and 24 hours, in independent runs. Total number of survivors is calculated for each cage. The results are shown in Table 15.

TABLE 15

| | Concentration | | | |
|---|---|---|---|---|
| | 5 ppm | | 1 ppm | |
| | 1h | 1h | 5h | 24h |
| | | mortality % | | |
| Ia | 100 | 100 | 100 | 96 |
| Ia:Ib = 4:6 | 100 | 50 | 90 | 63 |
| deltamethrin | 100 | 20 | 100 | 85 |

Example 29

Direct contact test on pupae of *A. metricariae*

Mature pupae of *A. matricariae* on paprika leaves in Petri-dishes are exposed to a direct spray of the active ingredients. Two or three days before emergence paprika leaves with parasitized pupae are used. The leaves are laid on moistened filter paper in a plastic Petri-dish.

Application of treatment: see Example 28.

The pieces of leaf are transferred after treatment to clean Petri-dish bottoms. The trays are stored in a climatic chamber at 20° C. temperature, 70% relative humidity and a light-dark cycle of 16-8 h. Surviving pupae hatch after 2-3 days. The numbers of hatched and dead pupae are counted. Results are shown in Table 16.

TABLE 16

| Active ingredient | Concentration | | | |
|---|---|---|---|---|
| | 30 ppm | 10 ppm | 5 ppm | 1 ppm |
| | mortality % | | | |
| Ib:Ia = 6:4 | 14.3 | 0 | 0 | 0 |
| Deltamethrin | 75.0 | 33.0 | 0 | 0 |
| Ia | 77.0 | 12.5 | 0 | 0 |
| control | 0 | 0 | 0 | 0 |

What we claim is:

1. An insecticidal composition, which comprises as active ingredient in an amount of 0.001-99% by weight a synthetic pyrethroid of the Formula I

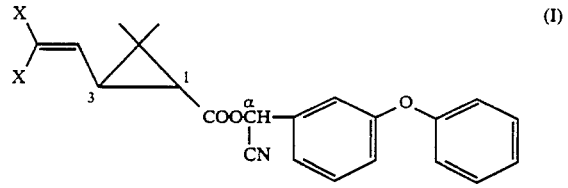

(I)

wherein X stands for chlorine—namely out of the eight possible isomers at least 95% of a 3:7 to 5:5 crystalline 1Mixture of the enantiomer pairs Ia:Ib, wherein Ia is 1RcisS+1ScisR and Ib is 1RtransR+1StransR—having a reduced mammalian toxicity by comparison with the enantiomer pair Ia and reduced toxicity to bees and a useful arthropod *Aphidinus matricuriae* by comparison with the enantiomer pair Ia.

2. The insecticidal composition defined in claim 1 which comprises as active ingredient a 40:60 mixture of Ia:Ib.

3. The insecticidal composition defined in claim 1 which comprises as active ingredient a 30:70 mixture of Ia:Ib.

4. The insecticidal composition defined in claim I which comprises as active ingredient a 50:50 mixture of Ia:Ib.

5. An insecticidal or acaricidal method of treatment which comprises applying to a site in need of insecticidal or acaricidal treatment, an insecticidally or acaricidally effective amount of the composition defined in claim 1 at a rate of 2 to 25 g of active ingredient per hectare.

* * * * *

UNITED STATES PATENT AND TRADEMARK OFFICE
CERTIFICATE OF CORRECTION

PATENT NO. : 4,963,584
DATED : 16 October 1990
INVENTOR(S) : György HIDASI etal

It is certified that error appears in the above-identified patent and that said Letters Patent is hereby corrected as shown below:

Col. 16:

Claim 1, line 7, for "1 Mixture" read -- mixture --; and line 8, for "1 RtransR" read -- 1 RtransS --.

Signed and Sealed this

Seventh Day of April, 1992

*Attest:*

HARRY F. MANBECK, JR.

*Attesting Officer*     *Commissioner of Patents and Trademarks*